(12) United States Patent
Hannula et al.

(10) Patent No.: US 8,483,790 B2
(45) Date of Patent: *Jul. 9, 2013

(54) NON-ADHESIVE OXIMETER SENSOR FOR SENSITIVE SKIN

(75) Inventors: Don Hannula, San Luis Obispo, CA (US); Paul D. Mannheimer, Danville, CA (US)

(73) Assignee: Covidien LP, Mansfield, MA (US)

( * ) Notice: Subject to any disclaimer, the term of this patent is extended or adjusted under 35 U.S.C. 154(b) by 1831 days.

This patent is subject to a terminal disclaimer.

(21) Appl. No.: 11/715,257

(22) Filed: Mar. 7, 2007

(65) Prior Publication Data

US 2007/0219440 A1 Sep. 20, 2007

Related U.S. Application Data

(63) Continuation of application No. 10/274,845, filed on Oct. 18, 2002, now Pat. No. 7,190,986.

(51) Int. Cl.
*A61B 5/1455* (2006.01)
(52) U.S. Cl.
USPC ............................ 600/344; 600/310; 600/323
(58) Field of Classification Search
USPC ................. 600/310, 322, 323, 324, 340, 344, 600/473, 476
See application file for complete search history.

(56) References Cited

U.S. PATENT DOCUMENTS

| | | | |
|---|---|---|---|
| 3,696,181 A | 10/1972 | Bonner, Jr. | |
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |

(Continued)

FOREIGN PATENT DOCUMENTS

| | | |
|---|---|---|
| DE | 19632361 | 2/1997 |
| EP | 0127947 | 12/1984 |

(Continued)

OTHER PUBLICATIONS

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

The present invention provides non-adhesive oximeter sensors for patients with sensitive skin. Sensors of the present invention include a light emitting diode (LED) and a photodetector. The LED and the photodetector may be covered by a reflective mask and a faraday shield. Sensors of the present invention have a non-adhesive laminated layer. The non-adhesive layer contacts, but does not stick to, the patient's skin. When the sensor is removed from the patient, the non-adhesive layer does not tear or irritate the patient's skin. The non-adhesive layer preferably has a large static coefficient of friction. Sensors of the present invention can also have hook-and-loop layers. The sensor can be attached to the patient's body by wrapping the sensor around the patient and engaging the hook layer to the loop layer.

10 Claims, 2 Drawing Sheets

U.S. PATENT DOCUMENTS

| | | | |
|---|---|---|---|
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,939,818 A * | 7/1990 | Hahn | 24/442 |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Freidman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Freidman et al. | |
| 5,311,865 A | 5/1994 | Mayeux | |
| 5,313,940 A | 5/1994 | Fuse et al. | |
| 5,323,776 A | 6/1994 | Blakely et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |

| | | | | | | |
|---|---|---|---|---|---|---|
| 5,398,680 A | 3/1995 | Polson et al. | | 5,662,106 A | 9/1997 | Swedlow et al. |
| 5,402,777 A | 4/1995 | Warring et al. | | 5,666,952 A | 9/1997 | Fuse et al. |
| 5,411,023 A | 5/1995 | Morris, Sr. et al. | | 5,671,529 A | 9/1997 | Nelson |
| 5,411,024 A | 5/1995 | Thomas et al. | | 5,673,692 A | 10/1997 | Schulze et al. |
| 5,413,099 A | 5/1995 | Schmidt et al. | | 5,673,693 A | 10/1997 | Solenberger |
| 5,413,100 A | 5/1995 | Barthelemy et al. | | 5,676,139 A | 10/1997 | Goldberger et al. |
| 5,413,101 A | 5/1995 | Sugiura | | 5,676,141 A | 10/1997 | Hollub |
| 5,413,102 A | 5/1995 | Schmidt et al. | | 5,678,544 A | 10/1997 | DeLonzor et al. |
| 5,417,207 A | 5/1995 | Young et al. | | 5,680,857 A | 10/1997 | Pelikan et al. |
| 5,421,329 A | 6/1995 | Casciani et al. | | 5,685,299 A | 11/1997 | Diab et al. |
| 5,425,360 A | 6/1995 | Nelson | | 5,685,301 A | 11/1997 | Klomhaus |
| 5,425,362 A | 6/1995 | Siker et al. | | 5,687,719 A | 11/1997 | Sato et al. |
| 5,427,093 A | 6/1995 | Ogawa et al. | | 5,687,722 A | 11/1997 | Tien et al. |
| 5,429,128 A | 7/1995 | Cadell et al. | | 5,692,503 A | 12/1997 | Kuenstner |
| 5,429,129 A | 7/1995 | Lovejoy et al. | | 5,692,505 A | 12/1997 | Fouts |
| 5,431,159 A | 7/1995 | Baker et al. | | 5,709,205 A | 1/1998 | Bukta |
| 5,431,170 A | 7/1995 | Mathews | | 5,713,355 A | 2/1998 | Richardson et al. |
| 5,437,275 A | 8/1995 | Amundsen et al. | | 5,724,967 A | 3/1998 | Venkatachalam |
| 5,438,986 A | 8/1995 | Disch et al. | | 5,727,547 A | 3/1998 | Levinson et al. |
| 5,448,991 A | 9/1995 | Polson et al. | | 5,731,582 A | 3/1998 | West |
| 5,452,717 A | 9/1995 | Branigan et al. | | D393,830 S | 4/1998 | Tobler et al. |
| 5,465,714 A | 11/1995 | Scheuing | | 5,743,260 A | 4/1998 | Chung et al. |
| 5,469,845 A | 11/1995 | DeLonzor et al. | | 5,743,263 A | 4/1998 | Baker, Jr. |
| RE35,122 E | 12/1995 | Corenman et al. | | 5,746,206 A | 5/1998 | Mannheimer |
| 5,474,065 A | 12/1995 | Meathrel et al. | | 5,746,697 A | 5/1998 | Swedlow et al. |
| 5,478,824 A | 12/1995 | Burns | | 5,752,914 A | 5/1998 | DeLonzor et al. |
| 5,482,034 A | 1/1996 | Lewis et al. | | 5,755,226 A | 5/1998 | Carim et al. |
| 5,482,036 A | 1/1996 | Diab et al. | | 5,758,644 A | 6/1998 | Diab et al. |
| 5,483,646 A | 1/1996 | Uchikoga | | 5,760,910 A | 6/1998 | Lepper, Jr. et al. |
| 5,485,847 A | 1/1996 | Baker, Jr. | | 5,766,125 A | 6/1998 | Aoyagi et al. |
| 5,490,505 A | 2/1996 | Diab et al. | | 5,766,127 A | 6/1998 | Pologe et al. |
| 5,490,523 A | 2/1996 | Isaacson et al. | | 5,769,785 A | 6/1998 | Diab et al. |
| 5,491,299 A | 2/1996 | Naylor et al. | | 5,772,587 A | 6/1998 | Gratton et al. |
| 5,494,032 A | 2/1996 | Robinson et al. | | 5,774,213 A | 6/1998 | Trebino et al. |
| 5,497,771 A | 3/1996 | Rosenheimer | | 5,776,058 A | 7/1998 | Levinson et al. |
| 5,499,627 A | 3/1996 | Steuer et al. | | 5,776,059 A | 7/1998 | Kaestle |
| 5,503,148 A | 4/1996 | Pologe et al. | | 5,779,630 A | 7/1998 | Fein et al. |
| 5,505,199 A | 4/1996 | Kim | | 5,779,631 A | 7/1998 | Chance |
| 5,507,286 A | 4/1996 | Solenberger | | 5,782,237 A | 7/1998 | Casciani et al. |
| 5,511,546 A | 4/1996 | Hon | | 5,782,756 A | 7/1998 | Mannheimer |
| 5,517,988 A | 5/1996 | Gerhard | | 5,782,757 A | 7/1998 | Diab et al. |
| 5,520,177 A | 5/1996 | Ogawa et al. | | 5,782,758 A | 7/1998 | Ausec et al. |
| 5,521,851 A | 5/1996 | Wei et al. | | 5,786,592 A | 7/1998 | Hök |
| 5,522,388 A | 6/1996 | Ishikawa et al. | | 5,790,729 A | 8/1998 | Pologe et al. |
| 5,524,617 A | 6/1996 | Mannheimer | | 5,792,052 A | 8/1998 | Isaacson et al. |
| 5,529,064 A | 6/1996 | Rall et al. | | 5,795,292 A | 8/1998 | Lewis et al. |
| 5,533,507 A | 7/1996 | Potratz et al. | | 5,797,841 A | 8/1998 | DeLonzor et al. |
| 5,551,423 A | 9/1996 | Sugiura | | 5,800,348 A | 9/1998 | Kaestle |
| 5,551,424 A | 9/1996 | Morrison et al. | | 5,800,349 A | 9/1998 | Isaacson et al. |
| 5,553,614 A | 9/1996 | Chance | | 5,803,910 A | 9/1998 | Potratz |
| 5,553,615 A | 9/1996 | Carim et al. | | 5,807,246 A | 9/1998 | Sakaguchi et al. |
| 5,555,882 A | 9/1996 | Richardson et al. | | 5,807,247 A | 9/1998 | Merchant et al. |
| 5,558,096 A | 9/1996 | Palatnik | | 5,807,248 A | 9/1998 | Mills |
| 5,560,355 A | 10/1996 | Merchant et al. | | 5,810,723 A | 9/1998 | Aldrich |
| 5,564,417 A | 10/1996 | Chance | | 5,810,724 A | 9/1998 | Gronvall |
| 5,575,284 A | 11/1996 | Athan et al. | | 5,813,980 A | 9/1998 | Levinson et al. |
| 5,575,285 A | 11/1996 | Takanashi et al. | | 5,817,008 A | 10/1998 | Rafert et al. |
| 5,577,500 A | 11/1996 | Potratz | | 5,817,009 A | 10/1998 | Rosenheimer et al. |
| 5,582,169 A | 12/1996 | Oda et al. | | 5,817,010 A | 10/1998 | Hibl |
| 5,584,296 A | 12/1996 | Cui et al. | | 5,818,985 A | 10/1998 | Merchant et al. |
| 5,588,425 A | 12/1996 | Sackner et al. | | 5,820,550 A | 10/1998 | Polson et al. |
| 5,588,427 A | 12/1996 | Tien | | 5,823,950 A | 10/1998 | Diab et al. |
| 5,590,652 A | 1/1997 | Inai | | 5,823,952 A | 10/1998 | Levinson et al. |
| 5,595,176 A | 1/1997 | Yamaura | | 5,827,182 A | 10/1998 | Raley et al. |
| 5,596,986 A | 1/1997 | Goldfarb | | 5,830,135 A | 11/1998 | Bosque et al. |
| 5,611,337 A | 3/1997 | Bukta | | 5,830,136 A | 11/1998 | DeLonzor et al. |
| 5,617,852 A | 4/1997 | MacGregor | | 5,830,137 A | 11/1998 | Scharf |
| 5,619,992 A | 4/1997 | Guthrie et al. | | 5,839,439 A | 11/1998 | Nierlich et al. |
| 5,626,140 A | 5/1997 | Feldman et al. | | RE36,000 E | 12/1998 | Swedlow et al. |
| 5,630,413 A | 5/1997 | Thomas et al. | | 5,842,979 A | 12/1998 | Jarman et al. |
| 5,632,272 A | 5/1997 | Diab et al. | | 5,842,981 A | 12/1998 | Larsen et al. |
| 5,632,273 A | 5/1997 | Suzuki | | 5,842,982 A | 12/1998 | Mannheimer |
| 5,634,459 A | 6/1997 | Gardosi | | 5,846,190 A | 12/1998 | Woehrle |
| 5,638,593 A | 6/1997 | Gerhardt et al. | | 5,851,178 A | 12/1998 | Aronow |
| 5,638,818 A | 6/1997 | Diab et al. | | 5,851,179 A | 12/1998 | Ritson et al. |
| 5,645,060 A | 7/1997 | Yorkey et al. | | 5,853,364 A | 12/1998 | Baker, Jr. et al. |
| 5,645,440 A | 7/1997 | Tobler et al. | | 5,860,919 A | 1/1999 | Kiani-Azarbayjany et al. |
| 5,660,567 A | 8/1997 | Nierlich et al. | | 5,865,736 A | 2/1999 | Baker, Jr. et al. |
| 5,662,105 A | 9/1997 | Tien | | 5,871,442 A | 2/1999 | Madarasz et al. |

| | | | | | | |
|---|---|---|---|---|---|---|
| 5,879,294 | A | 3/1999 | Anderson et al. | 6,122,535 A | 9/2000 | Kaestle et al. |
| 5,885,213 | A | 3/1999 | Richardson et al. | 6,133,994 A | 10/2000 | Mathews et al. |
| 5,890,929 | A | 4/1999 | Mills et al. | 6,135,952 A | 10/2000 | Coetzee |
| 5,891,021 | A | 4/1999 | Dillon et al. | 6,144,444 A | 11/2000 | Haworth et al. |
| 5,891,022 | A | 4/1999 | Pologe | 6,144,867 A | 11/2000 | Walker et al. |
| 5,891,024 | A | 4/1999 | Jarman et al. | 6,144,868 A | 11/2000 | Parker |
| 5,891,025 | A | 4/1999 | Buschmann et al. | 6,149,481 A | 11/2000 | Wang et al. |
| 5,891,026 | A | 4/1999 | Wang et al. | 6,150,951 A | 11/2000 | Olejniczak |
| 5,902,235 | A | 5/1999 | Lewis et al. | 6,151,107 A | 11/2000 | Schöllerman et al. |
| 5,910,108 | A | 6/1999 | Solenberger | 6,151,518 A | 11/2000 | Hayashi |
| 5,911,690 | A | 6/1999 | Rall | 6,152,754 A | 11/2000 | Gerhardt et al. |
| 5,912,656 | A | 6/1999 | Tham et al. | 6,154,667 A | 11/2000 | Miura et al. |
| 5,913,819 | A * | 6/1999 | Taylor et al. ............... 600/323 | 6,157,850 A | 12/2000 | Diab et al. |
| 5,916,154 | A | 6/1999 | Hobbs et al. | 6,163,715 A | 12/2000 | Larsen et al. |
| 5,916,155 | A | 6/1999 | Levinson et al. | 6,165,005 A | 12/2000 | Mills et al. |
| 5,919,133 | A | 7/1999 | Taylor et al. | 6,173,196 B1 | 1/2001 | Delonzor et al. |
| 5,919,134 | A | 7/1999 | Diab | 6,178,343 B1 | 1/2001 | Bindszus et al. |
| 5,920,263 | A | 7/1999 | Huttenhoff et al. | 6,181,958 B1 | 1/2001 | Steuer et al. |
| 5,921,921 | A | 7/1999 | Potratz et al. | 6,181,959 B1 | 1/2001 | Schöllerman et al. |
| 5,922,607 | A | 7/1999 | Bernreuter | 6,184,521 B1 | 2/2001 | Coffin, IV et al. |
| 5,924,979 | A | 7/1999 | Swedlow et al. | 6,188,470 B1 | 2/2001 | Grace |
| 5,924,980 | A | 7/1999 | Coetzee | 6,192,260 B1 | 2/2001 | Chance |
| 5,924,982 | A | 7/1999 | Chin | 6,195,575 B1 | 2/2001 | Levinson |
| 5,924,985 | A | 7/1999 | Jones | 6,198,951 B1 | 3/2001 | Kosuda et al. |
| 5,934,277 | A | 8/1999 | Mortz | 6,206,830 B1 | 3/2001 | Diab et al. |
| 5,934,925 | A | 8/1999 | Tobler et al. | 6,213,952 B1 | 4/2001 | Finarov et al. |
| 5,940,182 | A | 8/1999 | Lepper, Jr. et al. | 6,217,523 B1 | 4/2001 | Amano et al. |
| 5,954,644 | A | 9/1999 | Dettling et al. | 6,222,189 B1 | 4/2001 | Misner et al. |
| 5,960,610 | A | 10/1999 | Levinson et al. | 6,226,539 B1 | 5/2001 | Potratz |
| 5,961,450 | A | 10/1999 | Merchant et al. | 6,226,540 B1 | 5/2001 | Bernreuter et al. |
| 5,961,452 | A | 10/1999 | Chung et al. | 6,229,856 B1 | 5/2001 | Diab et al. |
| 5,964,701 | A | 10/1999 | Asada et al. | 6,230,035 B1 | 5/2001 | Aoyagi et al. |
| 5,971,930 | A | 10/1999 | Elghazzawi | 6,233,470 B1 | 5/2001 | Tsuchiya |
| 5,978,691 | A | 11/1999 | Mills | 6,236,871 B1 | 5/2001 | Tsuchiya |
| 5,978,693 | A | 11/1999 | Hamilton et al. | 6,236,872 B1 | 5/2001 | Diab et al. |
| 5,983,122 | A | 11/1999 | Jarman et al. | 6,240,305 B1 | 5/2001 | Tsuchiya |
| 5,987,343 | A | 11/1999 | Kinast | 6,253,097 B1 | 6/2001 | Aronow et al. |
| 5,991,648 | A | 11/1999 | Levin | 6,253,098 B1 | 6/2001 | Walker et al. |
| 5,995,855 | A | 11/1999 | Kiani et al. | 6,256,523 B1 | 7/2001 | Diab et al. |
| 5,995,856 | A | 11/1999 | Mannheimer et al. | 6,256,524 B1 | 7/2001 | Walker et al. |
| 5,995,858 | A | 11/1999 | Kinast | 6,261,236 B1 | 7/2001 | Grimblatov |
| 5,995,859 | A | 11/1999 | Takahashi | 6,263,221 B1 | 7/2001 | Chance et al. |
| 5,997,343 | A | 12/1999 | Mills et al. | 6,263,222 B1 | 7/2001 | Diab et al. |
| 5,999,834 | A | 12/1999 | Wang et al. | 6,263,223 B1 | 7/2001 | Sheperd et al. |
| 6,002,952 | A | 12/1999 | Diab et al. | 6,266,546 B1 | 7/2001 | Steuer et al. |
| 6,005,658 | A | 12/1999 | Kaluza et al. | 6,266,547 B1 | 7/2001 | Walker et al. |
| 6,006,120 | A | 12/1999 | Levin | 6,272,363 B1 | 8/2001 | Casciani et al. |
| 6,011,985 | A | 1/2000 | Athan et al. | 6,278,522 B1 | 8/2001 | Lepper, Jr. et al. |
| 6,011,986 | A | 1/2000 | Diab et al. | 6,280,213 B1 | 8/2001 | Tobler et al. |
| 6,014,576 | A | 1/2000 | Raley et al. | 6,280,381 B1 | 8/2001 | Malin et al. |
| 6,018,673 | A | 1/2000 | Chin et al. | 6,285,894 B1 | 9/2001 | Oppelt et al. |
| 6,018,674 | A | 1/2000 | Aronow | 6,285,895 B1 | 9/2001 | Ristolainen et al. |
| 6,022,321 | A | 2/2000 | Amano et al. | 6,285,896 B1 | 9/2001 | Tobler et al. |
| 6,023,541 | A | 2/2000 | Merchant et al. | 6,298,252 B1 | 10/2001 | Kovach et al. |
| 6,026,312 | A | 2/2000 | Shemwell et al. | 6,308,089 B1 | 10/2001 | Von der Ruhr et al. |
| 6,026,314 | A | 2/2000 | Amerov et al. | 6,321,100 B1 | 11/2001 | Parker |
| 6,031,603 | A | 2/2000 | Fine et al. | 6,330,468 B1 | 12/2001 | Scharf |
| 6,035,223 | A | 3/2000 | Baker, Jr. | 6,334,065 B1 | 12/2001 | Al-Ali et al. |
| 6,036,642 | A | 3/2000 | Diab et al. | 6,339,715 B1 | 1/2002 | Bahr et al. |
| 6,041,247 | A | 3/2000 | Weckstrom et al. | 6,343,223 B1 | 1/2002 | Chin et al. |
| 6,044,283 | A | 3/2000 | Fein et al. | 6,343,224 B1 | 1/2002 | Parker |
| 6,047,201 | A | 4/2000 | Jackson, III | 6,349,228 B1 | 2/2002 | Kiani et al. |
| 6,061,584 | A | 5/2000 | Lovejoy et al. | 6,351,658 B1 | 2/2002 | Middleman et al. |
| 6,064,898 | A | 5/2000 | Aldrich | 6,353,750 B1 | 3/2002 | Kimura et al. |
| 6,064,899 | A | 5/2000 | Fein et al. | 6,356,774 B1 | 3/2002 | Bernstein et al. |
| 6,067,462 | A | 5/2000 | Diab et al. | 6,360,113 B1 | 3/2002 | Dettling |
| 6,073,038 | A | 6/2000 | Wang et al. | 6,360,114 B1 | 3/2002 | Diab et al. |
| 6,078,833 | A | 6/2000 | Hueber | 6,361,501 B1 | 3/2002 | Amano et al. |
| 6,081,735 | A | 6/2000 | Diab et al. | 6,363,269 B1 | 3/2002 | Hanna et al. |
| 6,081,742 | A | 6/2000 | Amano et al. | 6,370,408 B1 | 4/2002 | Merchant et al. |
| 6,083,157 | A | 7/2000 | Noller | 6,370,409 B1 | 4/2002 | Chung et al. |
| 6,083,172 | A | 7/2000 | Baker, Jr. et al. | 6,374,129 B1 | 4/2002 | Chin et al. |
| 6,088,607 | A | 7/2000 | Diab et al. | 6,377,829 B1 | 4/2002 | Al-Ali et al. |
| 6,094,592 | A | 7/2000 | Yorkey et al. | 6,381,479 B1 | 4/2002 | Norris |
| 6,095,974 | A | 8/2000 | Shemwell et al. | 6,381,480 B1 | 4/2002 | Stoddar et al. |
| 6,104,938 | A | 8/2000 | Huiku et al. | 6,385,471 B1 | 5/2002 | Mortz |
| 6,112,107 | A | 8/2000 | Hannula | 6,385,821 B1 | 5/2002 | Modgil et al. |
| 6,113,541 | A | 9/2000 | Dias et al. | 6,388,240 B2 | 5/2002 | Schulz et al. |
| 6,115,621 | A | 9/2000 | Chin | 6,393,310 B1 | 5/2002 | Kuenster |

| | | |
|---|---|---|
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,479,015 B1 | 11/2002 | Long et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B1 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |

| Patent No. | Date | Inventor |
|---|---|---|
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Adbul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,341,559 B2 | 3/2008 | Schulz et al. |
| 7,369,886 B2 | 5/2008 | Delonzar et al. |
| 7,373,188 B2 | 5/2008 | Delonzar et al. |
| 7,373,189 B2 | 5/2008 | Delonzar et al. |
| 7,373,190 B2 | 5/2008 | Delonzar et al. |
| 7,373,191 B2 | 5/2008 | Delonzar et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |

| | | |
|---|---|---|
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276700 A1 | 12/2006 | O'Neil |
| 2007/0021659 A1 | 1/2007 | Delonzar et al. |
| 2007/0021660 A1 | 1/2007 | Delonzar et al. |
| 2007/0021662 A1 | 1/2007 | Delonzar et al. |
| 2007/0027378 A1 | 2/2007 | Delonzar et al. |
| 2007/0027379 A1 | 2/2007 | Delonzar et al. |
| 2007/0027380 A1 | 2/2007 | Delonzar et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |

FOREIGN PATENT DOCUMENTS

| | | |
|---|---|---|
| EP | 0204259 | 12/1986 |
| EP | 0531631 | 3/1993 |
| EP | 0724860 | 8/1996 |
| FR | 2685865 | 7/1993 |
| JP | 2111343 | 4/1990 |
| JP | 3116259 | 12/1991 |
| JP | 3116260 | 12/1991 |
| JP | 5049625 | 3/1993 |
| JP | 6014906 | 1/1994 |
| JP | 7001273 | 1/1995 |
| JP | 7236625 | 9/1995 |
| JP | 2000237170 | 9/2000 |
| JP | 2004089546 | 3/2004 |
| JP | 2004159810 | 6/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2000 |
| WO | WO0117421 | 3/2001 |
| WO | WO2005010567 | 2/2005 |

OTHER PUBLICATIONS

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Weil, Max Harry, et al.; "Sublingual Capnometry: A New Noninvasive Measurement for Diagnosis and Quantitation of Severity of Circulatory Shock"; Cirtical Care Medicine,vol. 27, No. 7 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

URL: http://www.cfw.com.my/fujifilm.html (2008).

\* cited by examiner

NON-ADHESIVE OXIMETER SENSOR FOR SENSITIVE SKIN

BACKGROUND OF THE INVENTION

The present application relates to non-adhesive oximeter sensors, and more particularly to non-adhesive oximeter sensors for patients with sensitive skin.

Non-invasive monitoring of a patient's pulse is common in medical practice. One type of pulse oximeter monitor incorporates one or more light-emitting-diodes (LEDs) to shine through an area of tissue containing large amounts of blood. The light source is mounted to well-perfused tissue, such as a fingertip. Light is emitted and shines through the tissue. The amount of light passing through the tissue is measured using a photodetector.

Changes between the light emitted by the light source and the light received by the photodetector are caused by changes in the optical absorption of the light by the blood perfusing through the monitored tissue. The LEDs can emit either broad-spectrum visual light or narrow bandwidth light in the red or infrared wavelengths.

The absorption of certain wavelengths is related to the oxygen saturation level of hemoglobin in the blood perfusing the tissue. The variations in light absorption caused by change in oxygen saturations make possible direct measurement of the arterial oxygen content.

One type of prior art oximeter sensor is the STAT-WRAP™ sensor E542 by Epic Medical Equipment Services of Plano, Tex. The STAT-WRAP™ sensor has a non-adhesive foam outer layer that contacts a patient's skin. The foam layer is a thick, bulky layer relative to the overall thickness of the sensor. The foam layer has a static coefficient of friction of about 1.43.

The STAT-WRAP™ sensor also has hook-and-loop layers that engage each other. The hook layer is a separate layer that is stitched to an end of the sensor.

Other prior art oximeter sensors have an outer adhesive layer. The adhesive layer is a sticky material that bonds temporarily to the skin like a band-aid. The adhesive holds the oximeter sensor on the skin of the patient so that it does not move or fall off, while measurements are being taken.

Some patients (e.g., neonates) have sensitive skin that may tear or become irritated when adhesive material is applied to the skin and later removed. It would therefore be desirable to provide an oximeter sensor that remains attached to a patient's skin without using adhesive material, while avoiding the bulk of prior-art non-adhesive sensors. It would further be desirable to accomplish these two features in a manner that the sensor can be sterilized and produced economically.

BRIEF SUMMARY OF THE INVENTION

The present invention provides non-adhesive oximeter sensors for patients with sensitive or fragile skin. Sensors of the present invention include a light emitting diode (LED) and a photodetector. The LED light shines light through a patient's tissue. The light from the LED is detected by the photodetector. The LED and photodetector may be covered by transparent windows. The LED and the photodetector may also be covered by a reflective mask and a Faraday electromagnetic shield.

Sensors of the present invention have a laminated non-adhesive layer. The non-adhesive layer contacts, but does not stick to, the patient's skin. When the sensor is removed from the patient, the non-adhesive layer does not tear or irritate the patient's skin. Therefore, the non-adhesive layer protects sensitive skin. In one embodiment, the non-adhesive layer is a polyvinyl chloride foam material. The non-adhesive layer preferably has a large static coefficient of friction to help keep the sensor motionless relative to the patient.

Sensors of the present invention also include one or more laminated layers that hold the sensor unit on the patient's body. These layers may include hook and loop layers. The sensor can be attached to the patient's body by wrapping the sensor around the patient and engaging the hook layer to the loop layer.

Sensors of the present invention may include a strengthening layer that lies between the other laminated layers. Furthermore, sensors of the present invention may include light-blocking features to minimize or eliminate ambient light interference and LED light from reaching the photodetector without passing through blood-perfused tissues (shunting).

DETAILED DESCRIPTION OF THE INVENTION

Figure 1A:
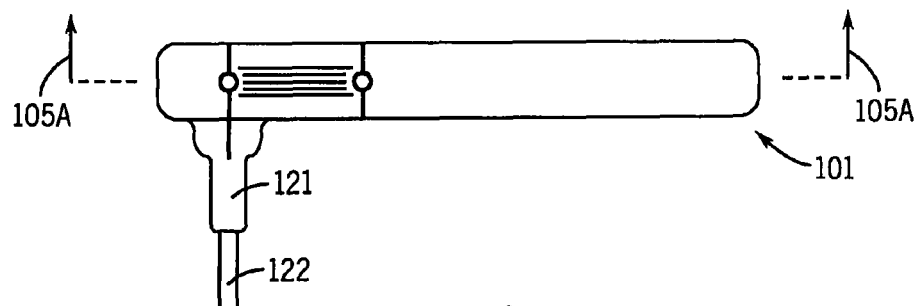
FIG. 1 illustrates cross sectional views of an embodiment of the non-adhesive oximeter sensor of the present invention.
Figure 1B:
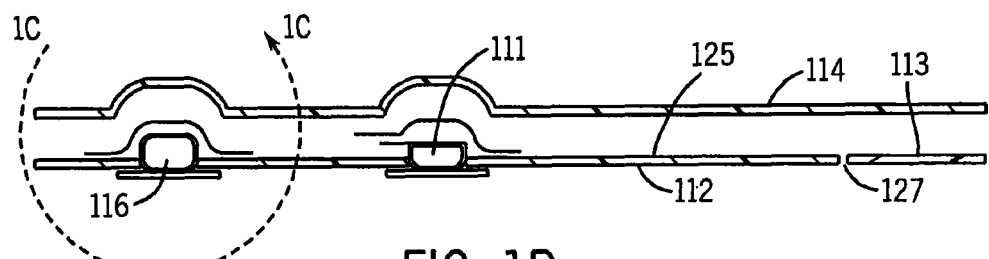
Figure 1C:
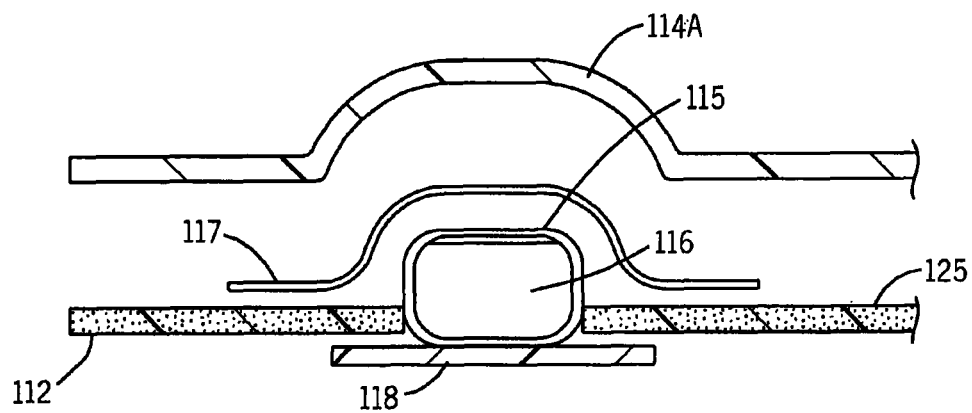

Oximeter sensor 101 shown in FIG. 1 is an embodiment of the present invention. A top down view of oximeter sensor 101 is shown in FIG. 1. A cross sectional view of oximeter sensor 101 along a plane 105A is also shown in FIG. 1. The cross sectional view shows the laminated layers of sensor 101. FIG. 1 also illustrates an expanded view 120 of a portion of the cross sectional view.

Oximeter sensor 101 has one or more light emitting diodes (LED) 111 and a photodetector 116 as shown in FIG. 1. LED 111 emits light that shines through a patient's tissue. The light from LED 111 is sensed by photodetector 116. Photodetector 116 produces a signal in response to the detected light. The signal is decoded by an oximeter monitor (not shown) to calculate the patient's blood oxygen saturation. LED 111 and photodetector 116 are connected to the oximeter monitor through wires that feed through cable 122.

Sensor 101 has a polyurethane window 118 below photodetector 116. Sensor 101 also has a polyurethane window below LED 111. The polyurethane windows are transparent. Light from LED 111 can pass unobstructed through the polyurethane windows to photodetector 116.

As shown in exploded view 120, photodetector 116 is surrounded by a reflective mask 117. Reflective mask 117 reflects light from LED 111 (that has passed through patient tissue and exited near the photodetector) back toward photodetector 116 like a mirror.

Reflective mask 117 increases the amount of LED light that the photodetector 116 receives from the patient's tissue, while assisting in blocking ambient light and LED light that may shunt through the laminated layers. LED 111 is also surrounded by a reflective mask that reflects light from LED 111 toward the patient's tissue. The reflective masks may comprise polyester or polypropylene with a reflective metal surface.

Photodetector 116 is also covered with a Faraday shield 115. Faraday shield 115 protects photodetector 116 from electromagnetic fields in the environment. Shield 115 reduces electromagnetic interference that may introduce noise into the output signal of photodetector 116.

Sensor 101 has laminated layers including layer 112 and hook-and-loop layers 113 and 114 shown in FIG. 1. Loop layer 114 has, for example, small loops of threads. Hook layer 113 has, for example, small hooks that engage with the loops in loop layer 114.

Hook layer 113 and loop layer 114 are used to attach sensor 101 to a patient. Hooks in hook layer 113 engage with the loops in loop layer 114. Once engaged, the hook-and-loop layers remain attached to each other, until they are pulled apart. The end user can engage and disengage hook layer 113 from loop layer 114 multiple times in order to open or close the fastener. One portion of layer 114 cannot attach to another portion of layer 114.

In one embodiment of the present invention, hook and loop layers 113 and 114 are VELCRO layers. In this embodiment, layer 114 comprises a VELCRO loop, and layer 113 comprises a VELCRO hook.

Loop layer 114 has a first raised portion 114A that provides room for the thickness of photodetector 116. Loop 114 also has a second raised portion that provides room for LED 111.

Sensor 101 also has a bottom laminated layer 112 as shown in FIG. 1. Layer 112 is a non-adhesive layer. Layer 112 is preferably made of a material that has a soft, smooth, non-skid surface. Layer 112 may, for example, comprise polyvinyl chloride (PVC) foam. One type of PVC that may be used with the present invention is 3M-9777L PVC foam manufactured by 3M Co. Layer 112 may also comprise other types of soft, non-adhesive material.

Bottom layer 112 is an outer layer of the sensor that contacts the patient's skin. Layer 112 comprises a non-adhesive material that does not adhere or stick to the patient's skin. Because layer 112 comprises a soft, non-adhesive material, it does not tear or irritate sensitive or fragile skin when sensor 101 is removed from the patient.

Layer 112 preferably comprises a material that has a relatively large static coefficient of friction. A material with a large static coefficient of friction helps to keep sensor 101 motionless relative to the skin as a patient moves. In sensors of the present invention, it is important to maximize the friction between the sensor and the skin, without the use of adhesives. Adhesives can damage fragile skin, and one objective of the present invention is to keep the sensor on the patient without slippage, but without the use of an adhesive.

According to the present invention, the static coefficient of friction of a material is tested using the following procedure. Attach a protractor to a vertical wall with the center in line with the edge of a table. Set up a stop block at the edge of the table to act as a pivot point for a glass plate. Place the glass plate flat on the table with one edge along the edge of the table, up against the stop block. Place a test sample of the material on the glass plate. Lift the free edge of the glass plate until the test sample just starts to slip. Record angle at which slippage first occurred. This angle is the angle of repose. Then calculate the coefficient of friction, which is the tangent of the angle of repose.

The coefficient of friction of polyvinyl chloride (PVC) foam is greater than the prior art foam wrap assembly found in the STAT-WRAP™ sensor. PVC foam measured using the above-described measuring technique resulted in a value of static coefficient of friction of infinity. The PVC foam actually stayed on the glass test plate even after achieving a 90 degree angle of repose.

The PVC material almost exhibits slight adhesive properties, surface tension forces, or static cling forces. Therefore, PVC foam is a very good choice of material for layer 112 in consideration of the preferred non-slip characteristics.

Materials other than PVC foam can be used for layer 112. The static coefficient of friction for layer 112 is preferably greater than 10. Most preferably, layer 112 has a static coefficient of friction that is greater than 100.

Layer 112 is preferably light in color to enhance the amplitude of the light signals received by photodetector 116. For example, layer 112 may be white, off-white, or cream colored. Alternatively, layer 112 may be dark in color to decrease the amount of ambient and shunted light that reaches the photodetector, at an expense of the amount of detected LED light signals.

Figure 2:
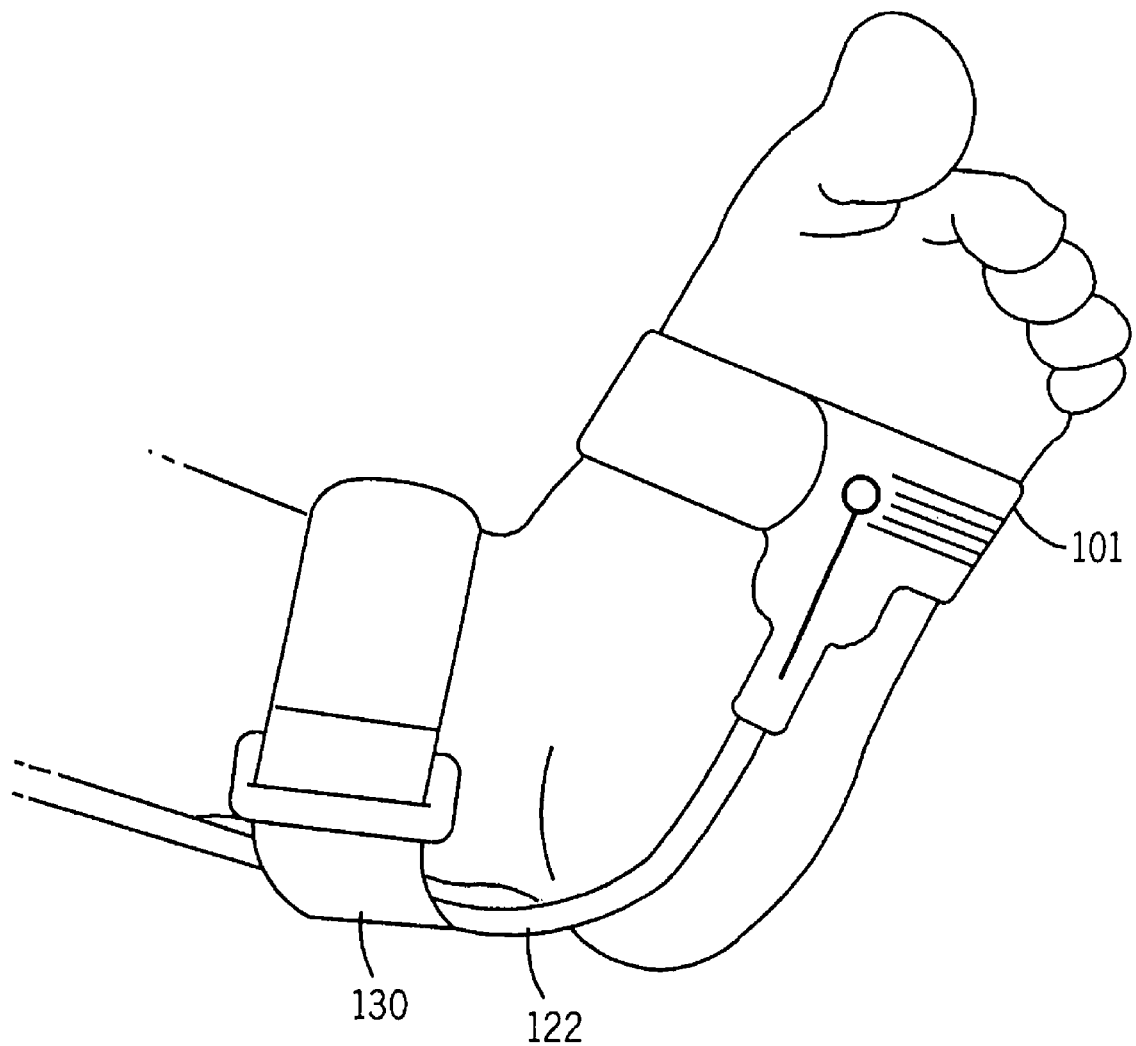
FIG. 2 illustrates how an embodiment of the non-adhesive oximeter sensor of the present invention can be placed on a patient's foot.

Layer 112 is preferably a thin layer, as shown in the cross sectional views in FIG. 1. By selecting a narrow thickness for layer 112, sensor 101 is less bulky. Because sensor 101 is thin, it is more flexible, and it can be easily conformed around a patient's body part. FIG. 2 illustrates an example of how sensor 101 can be placed around a patient's foot.

Sensor 101 may include an additional laminated layer. The additional laminated layer is a strengthening film (not shown) that lies between laminated layers 114 and 112. In one embodiment, hook layer 113 is attached to the strengthening film. In this embodiment, hook 113 is an integral part of one of the laminated layers that makes up the body of sensor 101. Hook portion 113 is not attached to layer 112. The foam layer 112 is discontinued at point 127 in FIG. 1, and hook portion 113 begins to the right of 127. In other embodiments, hook layer 113 is an integral part of bottom layer 112 or top layer 114.

In one embodiment of the present invention, the inner side 125 of layer 112 is covered with a laminated opaque film. The opaque film blocks ambient light that may interfere with photodetector 116. The opaque film may comprise polyethylene. The opaque film may be black or some other dark color that helps block ambient light and reduces shunted light. Dark in color is understood here to be of a nature with little reflectance of the wavelengths of light sensed by the sensor's photodetector.

Non-adhesive layer 112 is preferably long enough to wrap all the way around the patient's finger, toe, ear, or other portion of the body. Non-adhesive layer 112 is the only portion of sensor 101 that directly contacts the patient's skin. This feature of the present invention eliminates damage to the patient's skin that can be caused by adhesive portions of a sensor.

Once sensor 101 has been wrapped snuggly around the patient's finger, toe, or other body part, hook 113 is engaged with loop layer 114. Layer 114 is facing outward relative to the patient and does not contact the skin. Hook 113 engages with any portion of loop layer 114. The connection between hook 113 and loop 114 keeps sensor 101 firmly attached to the patient so that it does not fall off or move.

The laminated layers of sensor 101 are preferably thin layers. Non-adhesive layer 112 is preferably a thin, non-bulky layer. Because sensor 101 comprises thin laminated layers, sensor 101 has a low profile and can function much like a second skin. The laminated layers of sensor 101, when combined, are preferably less than 0.1 inches thick, and more preferably less than 0.75 inches thick.

Sensor 101 is also easily conformable to the shape of a patient's body part, because the laminated layers that make up sensor 101 are thin and flexible. Sensor 101 may be a single patient use (disposable) sensor.

Sensor 101, by virtue of the choice of materials used in the preferred embodiment and the simplicity of the lamination style construction, can be sterilized using conventional Ethylene Oxide (EO) methods and can be produced economically.

Sensor 101 can also have a portion 121 around the end of cable 122. Portion 121 includes loop material that wraps all the way around the circumference of cable 122 as shown in FIG. 1. Loop portion 121 provides additional area that hook 113 can attach to.

Referring again to FIG. 2, a strap 130 is attached to cable 122. Strap 130 includes hook-and-loop layers that engage each other. Strap 130 can be wrapped around a portion of the patient's body (e.g., the patient's ankle as shown in FIG. 2) to further secure sensor 101 to the patient. Strap 130 may be movably attached to cable 122 so that strap 130 can slide up and down the cable. This feature allows strap 130 to be placed at a position along cable 122 where it can be conveniently attached to the patient.

While the present invention has been described herein with reference to particular embodiments thereof, a latitude of modification, various changes, and substitutions are intended in the present invention. In some instances, features of the invention can be employed without a corresponding use of other features, without departing from the scope of the invention as set forth. Therefore, many modifications may be made to adapt a particular configuration or method disclosed, without departing from the essential scope and spirit of the present invention. It is intended that the invention not be limited to the particular embodiment disclosed, but that the invention will include all embodiments and equivalents falling-within the scope of the claims.

What is claimed is:

1. A sensor comprising:
   a light emitting element;
   a light detecting element;
   a substrate configured to encircle a portion of a patient, the substrate adapted to support the light emitting element and the light detecting element between layers, the substrate comprising a non-adhesive polyvinyl chloride material having a patient-contacting surface, the substrate having a thickness of less than 0.1 inch and being adapted to releasably attach one portion of the substrate to another portion of the substrate for securement to the patient, wherein the substrate comprises at least two layers laminated together;
   a cable coupled to the light emitting element and to the light detecting element; and
   a strap coupled to the cable, the strap being configured to wrap around a portion of the patient's body to secure the cable to the patient.

2. The sensor, as set forth in claim 1, wherein the strap is moveably coupled to the cable, the strap being configured to slide along the cable.

3. The sensor, as set forth in claim 1, wherein the at least one light emitting element and the at least one light detecting element are configured to produce oximetry readings.

4. The sensor, as set forth in claim 1, wherein the substrate comprises a non-adhesive patient contacting surface.

5. The sensor, as set forth in claim 1, wherein the substrate comprises a hook portion and a loop portion, the hook portion being releasably coupleable to the loop portion to facilitate attaching the substrate about an appendage of the patient.

6. The sensor, as set forth in claim 5, wherein the appendage comprises a foot.

7. The sensor, as set forth in claim 1, wherein the substrate comprises a plurality of thin layers of laminated material.

8. The sensor, as set forth in claim 1, wherein the strap comprises a loop at one end, the loop being secured around the cable to allow the strap to slide along the cable.

9. The sensor, as set forth in claim 1, wherein the strap comprises a hook portion and a loop portion, the hook portion being releasably coupleable to the loop portion to facilitate attaching the strap about the portion of the patient's body.

10. The sensor, as set forth in claim 9, wherein the portion of the patient's body comprises an ankle.

* * * * *